United States Patent
Park et al.

(10) Patent No.: US 12,178,628 B2
(45) Date of Patent: Dec. 31, 2024

(54) HAND-GRIP TYPE ORAL X-RAY DEVICE HAVING ALIGNMENT FUNCTION

(71) Applicant: NANORAY CO., LTD., Daegu (KR)

(72) Inventors: Jae Yoon Park, Gyeonggi-do (KR); Won Seong, Daejeon (KR)

(73) Assignee: NANORAY CO., LTD., Daegu (KR)

( * ) Notice: Subject to any disclaimer, the term of this patent is extended or adjusted under 35 U.S.C. 154(b) by 255 days.

(21) Appl. No.: 17/919,604

(22) PCT Filed: Oct. 26, 2020

(86) PCT No.: PCT/KR2020/014631
§ 371 (c)(1),
(2) Date: Oct. 18, 2022

(87) PCT Pub. No.: WO2022/034969
PCT Pub. Date: Feb. 17, 2022

(65) Prior Publication Data
US 2023/0165547 A1 Jun. 1, 2023

(30) Foreign Application Priority Data
Aug. 13, 2020 (KR) .......... 10-2020-0102085

(51) Int. Cl.
*A61B 6/51* (2024.01)
*A61B 6/00* (2024.01)

(52) U.S. Cl.
CPC .......... *A61B 6/512* (2024.01); *A61B 6/4405* (2013.01); *A61B 6/52* (2013.01)

(58) Field of Classification Search
CPC ......... A61B 6/512; A61B 6/4405; A61B 6/52; A61B 6/587; A61B 6/462; A61B 6/5205; A61B 6/56
See application file for complete search history.

(56) References Cited

U.S. PATENT DOCUMENTS

| | | | |
|---|---|---|---|
| 10,363,004 B2 * | 7/2019 | Holman | A61C 9/0053 |
| 2012/0064477 A1 * | 3/2012 | Schmitt | A61C 9/0053 433/44 |
| 2023/0172578 A1 * | 6/2023 | Park | A61B 6/4452 378/62 |

FOREIGN PATENT DOCUMENTS

| | | |
|---|---|---|
| JP | 2017-192412 A | 10/2017 |
| KR | 10-2014-0148247 A | 12/2014 |
| KR | 10-2018-0033106 A | 4/2018 |

(Continued)

OTHER PUBLICATIONS

International Search Report for PCT/KR2020/014631 mailed on May 4, 2021.

*Primary Examiner* — David P Porta
*Assistant Examiner* — Meenakshi S Sahu
(74) *Attorney, Agent, or Firm* — The PL Law Group, PLLC

(57) ABSTRACT

A hand-grip type oral X-ray device having an alignment function according to an embodiment includes an X-ray tube configured to generate and emit X-rays, an X-ray receiver including a first gyro-sensor and a first communication module, having, at a corner thereof, a magnet configured to generate a magnetic force, and configured to receive the X-rays generated from the X-ray tube to acquire X-ray data about an object in the oral cavity, and a handle including a rod-shaped grip operable by the hand of a user and an extension arm connecting the X-ray receiver and the grip to each other, and coupled to the X-ray receiver.

13 Claims, 6 Drawing Sheets

(56) References Cited

FOREIGN PATENT DOCUMENTS

| KR | 10-2018-0086850 A | 8/2018 |
|----|-------------------|--------|
| KR | 10-2085244 B1 | 3/2020 |

\* cited by examiner

HAND-GRIP TYPE ORAL X-RAY DEVICE HAVING ALIGNMENT FUNCTION

CROSS REFERENCE TO RELATED APPLICATIONS AND CLAIM OF PRIORITY

This application claims benefit under 35 U.S.C. 119, 120, 121, or 365 (c), and is a National Stage entry from International Application No. PCT/KR2020/014631, filed Oct. 26, 2020, which claims priority to the benefit of Korean Patent Application No. 10-2020-0102085 filed in the Korean Intellectual Property Office on Aug. 13, 2020, the entire contents of which are incorporated herein by reference.

BACKGROUND

1. Technical Field

The present disclosure relates generally to a hand-grip type oral X-ray device having an alignment function. More particularly, the present disclosure relates to a hand-grip type oral X-ray device for determining whether the oral X-ray device is aligned by using at least one sensor.

2. Background Art

Generally, in order to perform intraoral radiography on a subject in a dental clinic, etc., an intraoral X-ray sensor is engaged with an instrument called a sensor holder and then is inserted into the subject's oral cavity. After that, X-rays are emitted onto the intraoral X-ray sensor from an X-ray irradiation device provided outside the subject's oral cavity, whereby an intraoral structure between the X-ray irradiation device and the intraoral X-ray sensor is radiographed.

Here, the intraoral X-ray sensor is an image sensor that generates electric signals that projection data of the subject is reflected on by sensing X-rays having passed through the subject, and the sensor holder is an assistant tool configured to place the intraoral X-ray sensor at a desired location inside the subject's oral cavity and to align the intraoral X-ray sensor and the X-ray irradiation device to face each other along a straight line when it is necessary. In this regard, Korean Patent Publication 10-2018-0086850 will be described in detail as follows.

Korean Patent Publication 10-2018-0086850 relates to a sensor holder of an intraoral X-ray sensor. According to this, the sensor holder of the intraoral X-ray sensor having a front surface for receiving X-rays and a rear surface opposite to the front surface and including a fastener protruding rearward from the rear surface includes: a grip fitted over a side surface of the fastener and surrounding at least a portion of the side surface; a coupler connected to the grip and including a support facing in the forward direction of the intraoral X-ray sensor while covering at least parts of the rear surface and a side surface of the intraoral X-ray sensor; a connector connected to the support and extending in the forward direction of the intraoral X-ray sensor; and a handle connected to the connector.

However, according to Korean Patent Publication 10-2018-0086850 described above, in order to perform horizontal, lateral, and distance alignments between the intraoral X-ray sensor and an X-ray tube, it is cumbersome for a practitioner to visually check the horizontal, lateral, and distance states between the tube and the sensor and then manually move the sensor or tube to align them.

In addition, according to the Korean Patent Publication 10-2018-0086850 described above, when the horizontal, lateral, and distance alignments are made visually and manually, there is a problem in that the image magnification rate in the vertical, horizontal, or diagonal direction of an image is changed, and a final image of teeth is distorted from the original one. This increases the possibility that the practitioner who performs treatment on the basis of such a distorted image may make a misdiagnosis.

SUMMARY

An objective of the present disclosure is to provide a hand-grip type oral X-ray device having an alignment function, in which an X-ray tube and an oral X-ray sensor device are each equipped with at least one sensor including a gyro-sensor to check whether the oral X-ray sensor device is aligned.

Another objective of the present disclosure is to provide a hand-grip type oral X-ray device that allows a user to use the device in a hand-grip method without the use of a cable, and has an X-ray sensor and an X-ray image generating program built therein to allow the user to immediately ascertain a radiographic image after radiography.

In order to accomplish the above objective,
the present disclosure provides a hand-grip type oral X-ray device having an alignment function, the hand-grip type oral X-ray device including: an X-ray tube configured to generate and emit X-rays;
an X-ray receiver including a first gyro-sensor and a first communication module, having, at a corner thereof, a magnet configured to generate a magnetic force, and configured to receive the X-rays generated from the X-ray tube to acquire X-ray data about an object in an oral cavity; and
a handle including a rod-shaped grip operable by a hand of a user and an extension arm connecting the X-ray receiver and the grip to each other, and coupled to the X-ray receiver, wherein the handle may include: an image generating unit
configured to process a radiographic image taken by the X-ray receiver through a radiographic image processing program to generate a radiographic image file in a form that can be visually ascertained by the user;
a first display unit configured to display the radiographic image generated by the image generating unit;
a memory unit configured to store the radiographic image taken by the X-ray receiver; and
a power supply unit configured to supply power to the X-ray receiver and the handle,
and the X-ray tube may include: a second gyro-sensor;
a Hall sensor configured to sense the magnetic force formed by the magnet;
an ultrasonic sensor configured to sense the X-ray receiver by generating ultrasonic waves; and
a proximity sensor configured to sense a distance between the X-ray tube and the X-ray receiver.

Furthermore, in the hand-grip type oral X-ray device having the alignment function, the X-ray tube may include a second communication module for bidirectional communication with the first communication module, and
the first communication module and the second communication module may use a Bluetooth or Wi-Fi type wireless short-range communication protocol.

Furthermore, in the hand-grip type oral X-ray device having the alignment function, the X-ray tube may include: an alignment check unit configured to check whether position, lateral, distance, and horizontal alignments between the X-ray tube and the X-ray receiver have been made; and a second display unit configured to display information of whether the position, lateral, distance, and horizontal alignments between the X-ray tube and the X-ray receiver have been made.

Furthermore, in the hand-grip type oral X-ray device having the alignment function, the alignment check unit may determine whether the horizontal alignment between the X-ray receiver and the X-ray tube has been made on the basis of data sensed by the first gyro-sensor and the second gyro-sensor.

Furthermore, in the hand-grip type oral X-ray device having the alignment function, the alignment check unit may sense the X-ray receiver through the ultrasonic waves emitted from the ultrasonic sensor to determine whether the position alignment of the X-ray receiver has been made.

Furthermore, in the hand-grip type oral X-ray device having the alignment function, the alignment check unit may sense the magnetic force generated from the magnet to determine whether the lateral alignment of the X-ray receiver has been made.

Furthermore, in the hand-grip type oral X-ray device having the alignment function, the alignment check unit may sense the distance between the X-ray tube and the X-ray receiver through the proximity sensor to determine whether the distance alignment of the X-ray receiver has been made.

Furthermore, the hand-grip type oral X-ray device having the alignment function may further include a sensor coupler connecting the handle and the X-ray receiver to each other, wherein the sensor coupler may have a hinge structure that allows the X-ray receiver to be rotated in left and right directions relative to the handle.

Furthermore, the hand-grip type oral X-ray device having the alignment function may further include a sensor coupler connecting the handle and the X-ray receiver to each other, wherein the sensor coupler may be configured in the form of a ball stud for ball joint at a side of the handle, the X-ray receiver may be provided on an inner side of a surface thereof with a bearing coupled to the ball stud, and the ball stud and the bearing may be coupled to allow the X-ray receiver to be rotatable relative to the handle.

Furthermore, in the hand-grip type oral X-ray device having the alignment function, the sensor coupler may have a hinge structure that allows the X-ray receiver to be rotated in a range of 90 degrees to −90 degrees relative to the handle.

Furthermore, in the hand-grip type oral X-ray device having the alignment function, the handle may include at least one of a configuration in which a part or entirety of the grip is configured to be bendable and a configuration in which the extension arm is configured to be bendable.

Furthermore, in the hand-grip type oral X-ray device having the alignment function, the power supply unit may be configured by selecting any one of a a battery and supercapacitor, and
the power supply unit may include a power charging unit configured to charge the power supply unit.

According to the present disclosure, a patient or a practitioner only needs to place and fix a sensor at a desired location where radiography is to be performed while holding a handle, so there is no need for the patient or practitioner to insert the hand into the oral cavity. Thus, the radiography can be performed in a sanitary manner.

Furthermore, according to the embodiment of the present disclosure, information of whether horizontal, lateral, position, and distance alignments of an X-ray sensor device have been made is displayed on a display through the sensor to allow the patient or practitioner to ascertain the information, an image having a constant magnification can be obtained by performing radiography in a state in which the X-ray sensor device is aligned, and the amount of radiation exposure for the patient or practitioner can be minimized by preventing repeated re-radiography.

Furthermore, according to the present disclosure, the patient or practitioner fixes the sensor while holding the long handle of the X-ray sensor device, so it is easy for the patient or practitioner to place the sensor at the desired location more accurately. Also, the patient or practitioner holds the handle with the entire hand during the radiography, so the sensor can be stably placed at the desired location without undergoing a change in position.

Furthermore, according to the present disclosure, it is possible to implement a wireless method without a cable connected to the sensor or to store an image taken by the sensor in a memory device connected to the sensor. This eliminates discomfort experienced by the patient or practitioner due to the use of the cable connected to the sensor.

In addition, according to the present disclosure, the X-ray sensor device has a built-in function for generating a radiographic image, so the patient or practitioner can immediately ascertain the radiographic image after the radiography through the built-in function of the X-ray sensor device and an image display device without the need to move the X-ray sensor device to another place to ascertain the radiographic image after the radiography.

DETAILED DESCRIPTION

Figure 1:
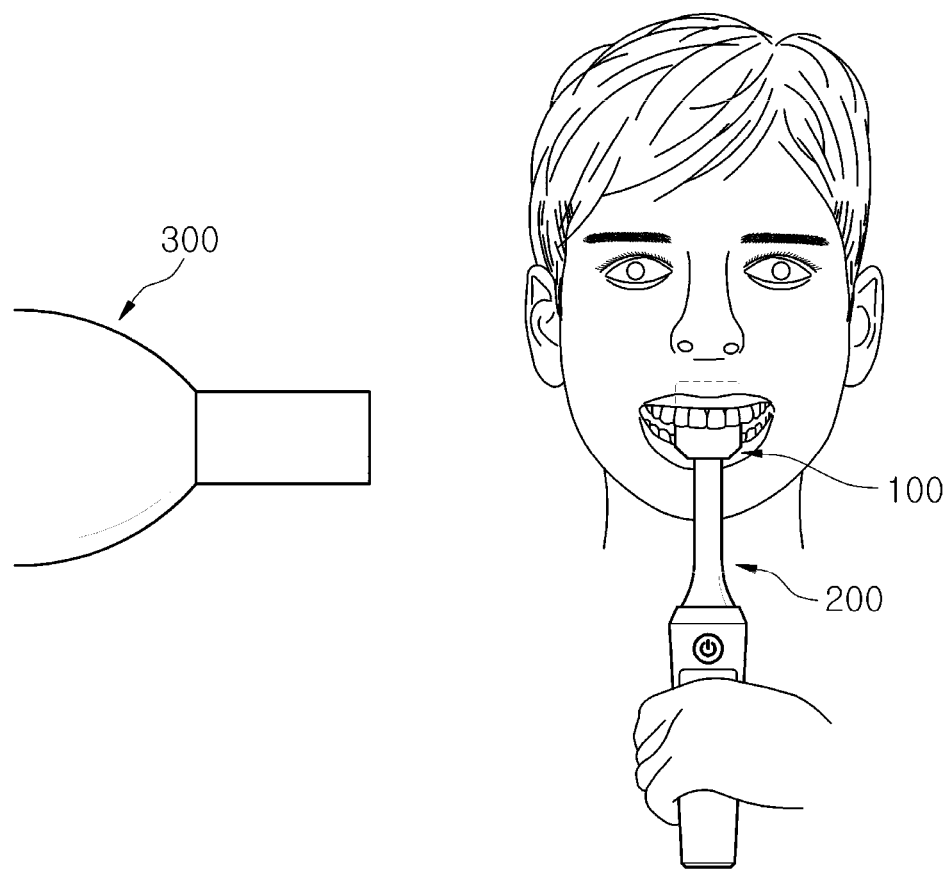
FIG. 1 is an exemplary view illustrating a use state of a hand-grip type oral X-ray device having an alignment function according to an embodiment of the present disclosure.
Figure 2:
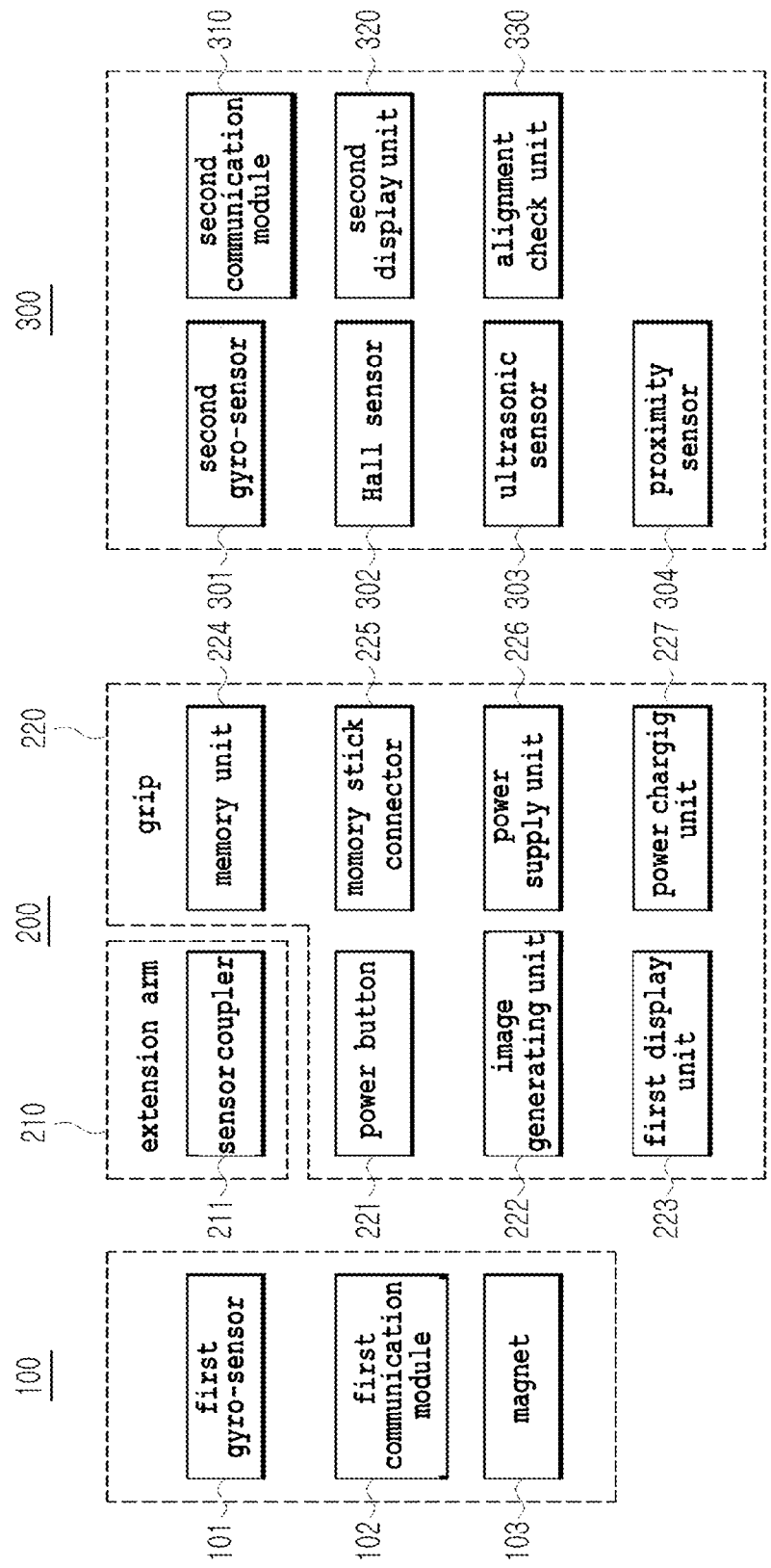
FIG. 2 is a block diagram illustrating the hand-grip type oral X-ray device having the alignment function according to the embodiment of the present disclosure.
Figure 3:
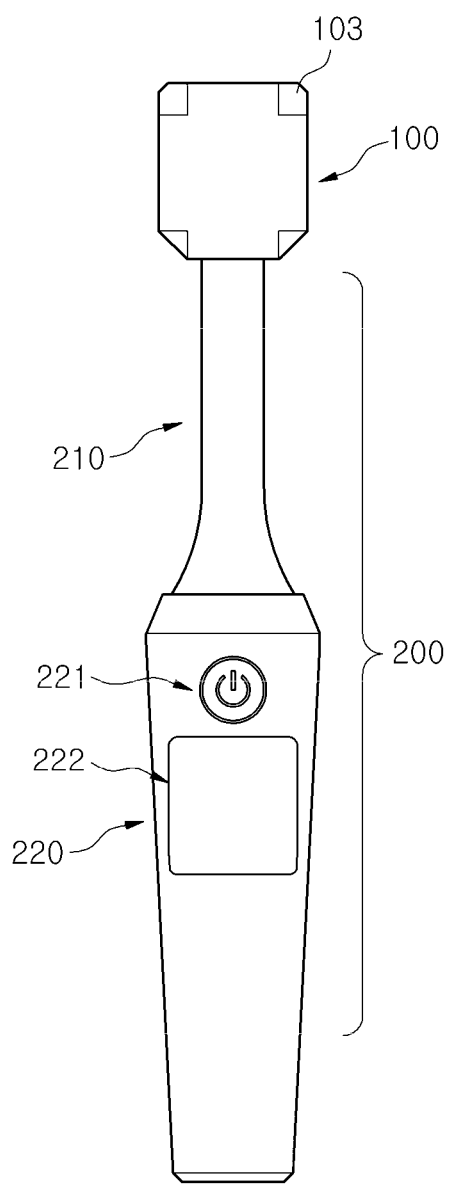
FIG. 3 is a front view illustrating the hand-grip type oral X-ray device having the alignment function according to the embodiment of the present disclosure.

As illustrated in FIGS. 1 to 3, a hand-grip type oral X-ray device having an alignment function according to an embodiment of the present disclosure may include an X-ray receiver 100, a handle 200, and an X-ray tube 300.

The X-ray tube 300 is a device that generates X-rays and emits the X-rays onto the X-ray receiver 100, and may include a sensor unit, a second communication module 310, a second display unit 320, and an alignment check unit 330.

The X-ray receiver 100 may acquire X-ray data of an object in the oral cavity by receiving X-rays generated from the X-ray tube 300, and transmit the acquired X-ray data to the X-ray tube 300 or a separate medical server (not illustrated) through the second communication module 310.

Here, a first communication module 102 built in the X-ray receiver 100 and the second communication module 310 built in the X-ray tube 300 may be configured to enable two-way communication, and may establish two-way communication using a Bluetooth or Wi-Fi type wireless short-range communication protocol. The second communication module 310 may additionally establish a communication network using the medical server and the wireless short-range communication protocol.

The X-ray receiver 100 may have a first gyro sensor 101 built therein and may have a polygonal shape. The X-ray receiver 100 may be configured to generate a magnetic force by having a magnet 103 at a corner thereof.

One or more magnets 103 may be installed at corners of the X-ray receiver 100 and may function to generate a magnetic force so that a Hall sensor 302 installed in the X-ray tube 300 senses the magnetic force. For example, when the X-ray receiver 100 is formed in a quadrangular shape, four magnets 103 may be installed at respective corners thereof.

The X-ray tube 300 may additionally function to determine whether horizontal, distance, position, and lateral alignments of the X-ray receiver 100 have been made. Specifically, the X-ray tube 300 may have at least one sensor unit 301, 302, 303, and 304 built therein to collect information of the X-ray receiver 100, and may further include the alignment check unit 330 checking whether the alignments of the X-ray receiver 100 have been made on the basis of the information collected by the sensor unit and the second display unit 320 for displaying information determined by the alignment check unit 330.

The sensor unit may include a second gyro-sensor 301, a Hall sensor 302, an ultrasonic sensor 303, and a proximity sensor 304, and may collect information necessary for the horizontal, distance, position and lateral alignments of the X-ray receiver 100 by utilizing the above-described sensors. A separate sensor may be additionally installed to collect information necessary for the alignments of the X-ray receiver 100.

The second gyro-sensor 301 may collect information together with the first gyro-sensor 101 installed in the X-ray receiver 100 and transmit the collected data to the alignment check unit 330. The alignment check unit 330 may determine whether the horizontal alignment between the X-ray receiver 100 and the X-ray tube 300 has been made on the basis of the information provided by the first gyro-sensor 101 and the second gyro-sensor 301, and display the determined information on the second display unit 320.

The Hall sensor 302 may sense the magnetic force generated from the magnets 103 to collect information of the left and right sides of the X-ray receiver 100, and transmit the collected data to the alignment check unit 330. The alignment check unit 330 may determine whether the lateral alignment between the X-ray receiver 100 and the X-ray tube 300 has been made on the basis of the information collected by the Hall sensor 302, and display the determined information on the second display unit 320.

The ultrasonic sensor 303 may emit ultrasonic waves to collect information of the position of the X-ray receiver 100, and transmit the collected data to the alignment check unit 330. The alignment check unit 330 may determine whether the position alignment between the X-ray receiver 100 and the X-ray tube 300 has been made on the basis of the information collected by the ultrasonic sensor 303, and display the determined information on the second display unit 320.

The proximity sensor 304 may collect information of the distance between the X-ray receiver 100 and the X-ray tube 300 and transmit the collected data to the alignment check unit 330. The alignment check unit 330 may determine whether the distance alignment between the X-ray receiver 100 and the X-ray tube 300 has been made on the basis of the information collected by the proximity sensor 304, and display the determined information on the second display unit 320.

In other words, the alignment check unit 330 may determine whether the horizontal, lateral, position, and distance alignments of the X-ray receiver 100 have been made on the basis of the information collected by the sensor unit 301, 302, 303, and 304, and display the determined information on the second display unit 320. Here, information of the alignment which has been completed and information of the alignment which has not been completed may be displayed separately.

For example, when the horizontal, lateral, position, and distance alignments are completed, a pop-up message indicating that radiography is allowed to be performed may be displayed, and when any one of the above four alignment criteria is not satisfied, a pop-up message related to alignment mismatch may be displayed. These messages may be controlled and managed by the alignment check unit 330.

In addition, the handle 200 may be configured to extend on a surface of the X-ray receiver 100.

The handle 200 may be formed in a long rod shape that is operable by the hand of a user while fixing the X-ray receiver 100.

The handle 200 may include a grip 220 operable by the user's hand, and an extension arm 210 connecting the X-ray receiver 100 to the grip 220. In the embodiment of the present disclosure, the handle 200 has been described as being composed of the grip 220 and the extension arm 210 as an example, but the present disclosure is not limited thereto. For example, the handle 200 may be formed as a single body, and may be implemented in various other forms or shapes as long as it has a shape device that is operable by a patient or a practitioner. These various embodiments should be considered to be within the scope of the present disclosure as long as they have a structure in which the rod-shaped handle 200 connected to a sensor is operable by the patient or practitioner.

A part or entirety of the handle 200 may be made of a bendable material. More specifically, the extension arm 210 may be configured to be bendable, or a part or entirety of the grip 220 may be configured to be bendable. When the handle 200 has a bendable structure in these various ways, the angle of the X-ray receiver 100 may be easily adjusted.

In addition, an image generating unit 222 may be built in the handle 200. The image generating unit 222 may process a radiographic image taken by the X-ray receiver 100 through a radiographic image processing program to convert the image into a radiographic image file in a form that can be visually ascertained by the user. The radiographic image processing program is a program for processing X-ray data obtained from the X-ray receiver 100 into a radiographic image file in a form that can be visually ascertained by the user, and a further detailed description thereof will be omitted because it is well-known to those skilled in the art.

A first display unit 223 for displaying the radiographic image generated by the image generating unit 222 may be additionally installed at the handle 200. The first display unit 223 may be installed at a predetermined position on the grip 220 or the handle 200. In the embodiment of the present disclosure, an LCD display or an OLED display may be mounted on an upper side surface of the grip 220, and various display technologies other than LCD and OLED display technologies may be employed.

The handle 200 may be provided with a memory unit 224 for storing the radiographic image file converted by the image generating unit 222. In addition, a memory stick connector 225 into which a memory stick is inserted may be provided at a predetermined position on the handle 200 so that data stored in the memory unit 224 is downloaded from the outside. The memory stick may be a memory card or a USB memory, and may include various information storage devices. In addition, the memory stick connector 225 may be a memory card socket or a USB connector.

The handle 200 may be provided at a side thereof with a power button 221 for turning power on/off, and may have an LED element built therein to display a power state and an operating state of an X-ray device (the X-ray receiver 100 and the handle 200).

In addition, the handle 200 may have a power supply unit 226 built therein to supply power to components included in the X-ray receiver 100 and the handle 200. The power supply unit 226 may include a battery or a supercapacitor, and may be provided with a power charging unit 227 for charging the battery or supercapacitor. The power charging unit 227 may be provided at the same position as the memory stick connector 225 to simultaneously use an image transmission/reception function and a power charging function, but is not limited thereto, and may be separately provided at a predetermined position on the handle 200 to separately charge the power supply unit 226.

Figure 4:
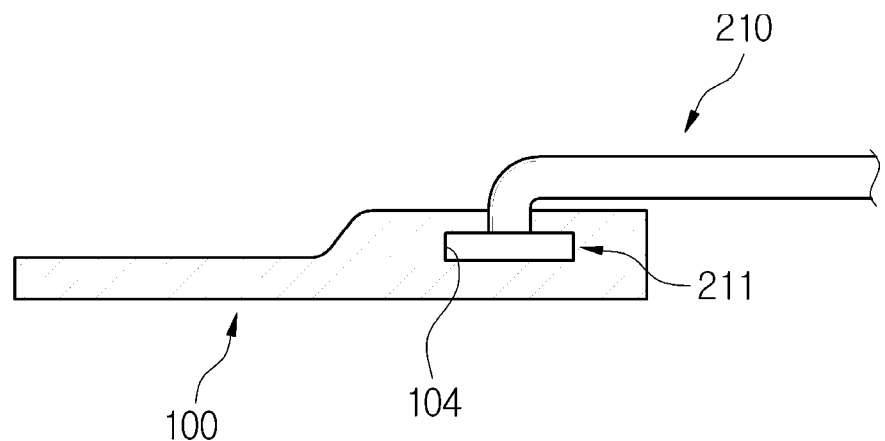
FIG. 4 is a sectional view illustrating a fastening state of an X-ray receiver and a handle of a hand-grip type oral X-ray device having an alignment function according to another embodiment of the present disclosure.
Figure 5:
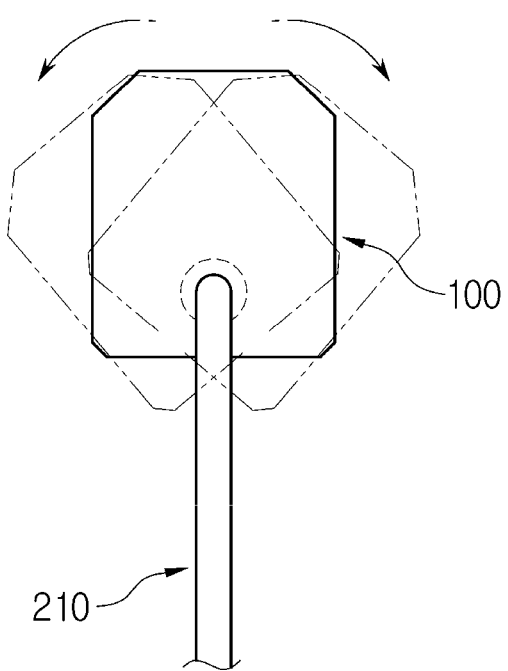
FIG. 5 is a rear view illustrating an operating state of the X-ray receiver of the hand-grip type oral X-ray device having the alignment function according to the other embodiment of the present disclosure.

As illustrated in FIGS. 4 and 5, a hand-grip type oral X-ray device having an alignment function according to another embodiment of the present disclosure may include may have a structure in which a sensor coupler 211 located at an end of a handle 200 is coupled to an X-ray receiver 100 by a hinge method.

The sensor coupler 211 may be formed in a disc shape. A fastening hole 104 may be formed in the X-ray receiver 100 to allow the disc-shaped sensor coupler 211 seated inside the X-ray receiver 100. The disc-shaped sensor coupler 211 may be inserted into the X-ray receiver 100. The X-ray receiver 100 may be implemented in a form rotatable relative to the handle 200. That is, the sensor coupler 211 may have a hinge structure that allows the X-ray receiver 100 to be rotated in left and right directions relative to the handle 200.

Furthermore, the sensor coupler 211 may be integrally configured with the handle 200, and may be made of the same material as the handle 200, but may be configured as a separate part made of a material different from the handle 200 if necessart.

In other words, according to the other embodiment of the present disclosure, the sensor coupler 211 and the X-ray receiver 100 may be simply coupled through an engagement between the disc-shaped coupler 211 and the hole 104. Various types of mechanical configurations in which the X-ray receiver 100 is rotatable relative to the handle 200 are possible, and these mechanical configurations should be considered to be within the scope of the present disclosure.

Figure 6:
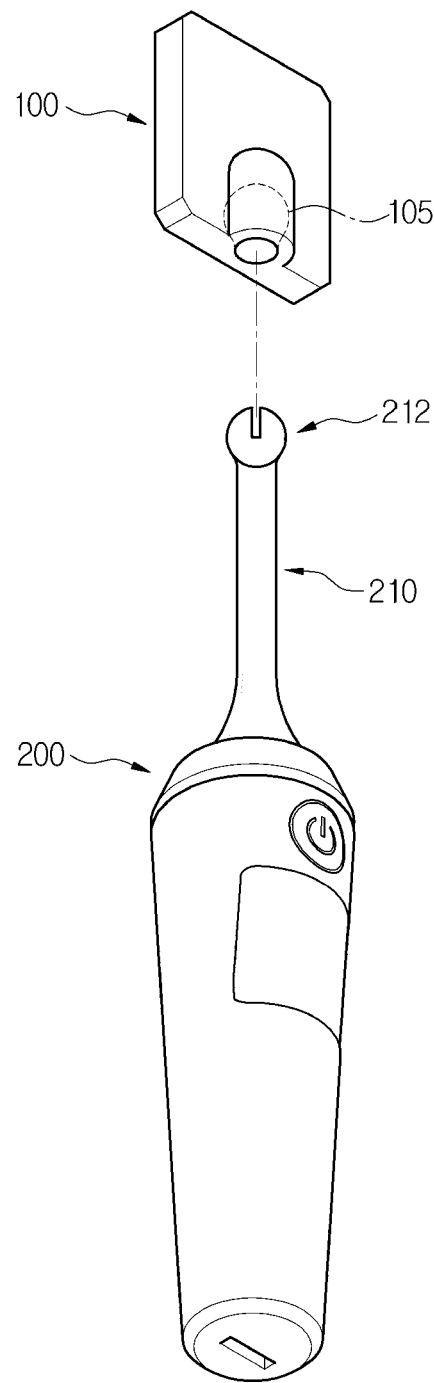
FIGS. 6 and 7 are a partial exploded perspective view and a perspective view illustrating a coupling state of a hand-grip type oral X-ray device having an alignment function according to another embodiment of the present disclosure.
Figure 7:
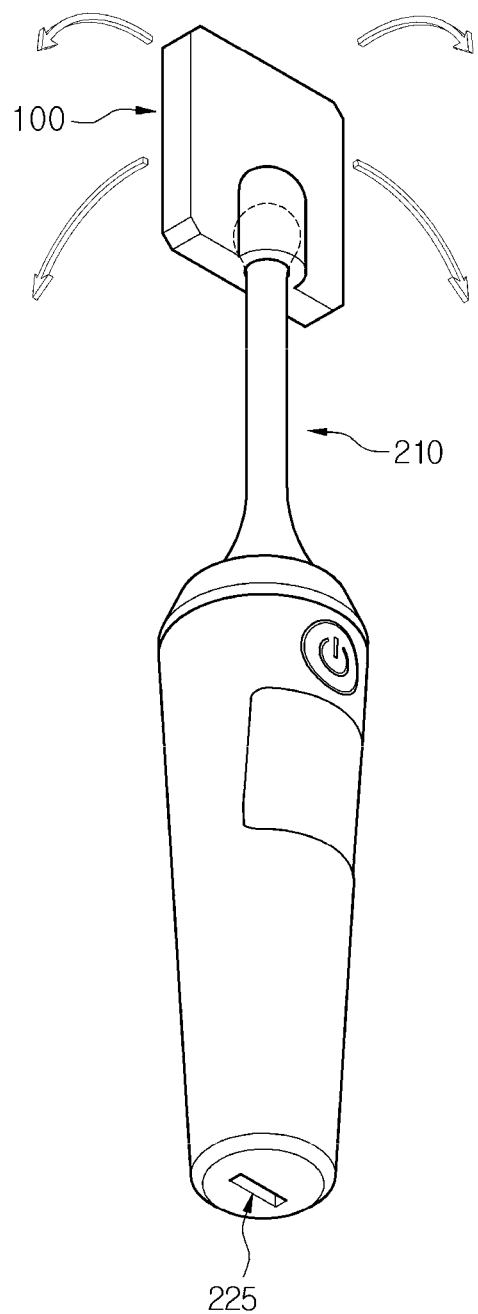

As illustrated in FIGS. 6 and 7, a hand-grip type oral X-ray device having an alignment function according to another embodiment of the present disclosure may have a structure in which a sensor coupler 212 located at an end of a handle 200 is coupled to an X-ray receiver 100 by a ball joint method so that X-ray receiver 100 is capable of rotational movement including pitching, rolling, and yawing relative to the handle 200.

The sensor coupler 212 may be configured in the form of a ball stud for ball joint at a side of an extension arm 210. The X-ray receiver 100 may further include a bearing 105 coupled to the ball stud on a surface thereof opposite to a surface thereof where a sensor for taking a radiographic image in the oral cavity. The ball stud and the bearing 105 may be coupled to allow the X-ray receiver 100 to be rotatable about the sensor coupler 212.

Furthermore, the sensor coupler 212 may be integrally configured with the handle 200, and may be made of the same material as the handle 200, but may be configured as a separate part made of a material different from the handle 200 if necessary.

A hand-grip type oral X-ray device having an alignment function according to the present disclosure can easily perform radiography of teeth during dental treatment and, in particular, can be used for the purpose of quick and convenient alignment of the device during radiography.

What is claimed is:

1. A hand-grip type oral X-ray device having an alignment function, the hand-grip type oral X-ray device comprising:
    an X-ray tube configured to generate and emit X-rays;
    an X-ray receiver comprising a first gyro-sensor, first communication module, and a magnet positioned at a corner of the X-ray receiver, configured to generate a magnetic force, the X-ray receiver configured to receive the X-rays generated from the X-ray tube to acquire X-ray data about an object in an oral cavity; and
    a handle comprising a rod-shaped grip operable by a hand of a user and an extension arm connecting the X-ray receiver and the grip to each other, the handle coupled to the X-ray receiver,
    wherein the handle comprises:
        an image generating unit configured to process a radiographic image taken by the X-ray receiver through a radiographic image processing program to generate a radiographic image file in a form that can be visually ascertained by the user;
        a first display unit configured to display the radiographic image generated by the image generating unit;
        a memory unit configured to store the radiographic image taken by the X-ray receiver; and
        a power supply unit configured to supply power to the X-ray receiver and the handle, wherein the X-ray tube comprises:
        a second gyro-sensor;
        a Hall sensor configured to sense the magnetic force formed by the magnet;
        an ultrasonic sensor configured to sense the X-ray receiver by generating ultrasonic waves; and
        a proximity sensor configured to sense a distance between the X-ray tube and the X-ray receiver.

2. The hand-grip type oral X-ray device of claim 1, wherein the X-ray tube comprises a second communication module for bidirectional communication with the first communication module, and the first communication module and the second communication module use a Bluetooth or Wi-Fi type wireless short-range communication protocol.

3. The hand-grip type oral X-ray device of claim 1, wherein the X-ray tube comprises:

an alignment check unit configured to check whether position, lateral, distance, and horizontal alignments between the X-ray tube and the X-ray receiver have been made; and a second display unit configured to display information of whether the position, lateral, distance, and horizontal alignments between the X-ray tube and the X-ray receiver have been made.

4. The hand-grip type oral X-ray device of claim 3, wherein the alignment check unit determines whether the horizontal alignment between the X-ray receiver and the X-ray tube has been made on the basis of data sensed by the first gyro-sensor and the second gyro-sensor.

5. The hand-grip type oral X-ray device of claim 3, wherein the alignment check unit senses the X-ray receiver through the ultrasonic waves emitted from the ultrasonic sensor to determine whether the position alignment of the X-ray receiver has been made.

6. The hand-grip type oral X-ray device of claim 3, wherein the alignment check unit senses the magnetic force generated from the magnet to determine whether the lateral alignment of the X-ray receiver has been made.

7. The hand-grip type oral X-ray device of claim 3, wherein the alignment check unit senses the distance between the X-ray tube and the X-ray receiver through the proximity sensor to determine whether the distance alignment of the X-ray receiver has been made.

8. The hand-grip type oral X-ray device of claim 1, further comprising a sensor coupler connecting the handle and the X-ray receiver to each other, wherein the sensor coupler has a hinge structure that allows the X-ray receiver to be rotated in left and right directions relative to the handle.

9. The hand-grip type oral X-ray device of claim 1, further comprising a sensor coupler connecting the handle and the X-ray receiver to each other, wherein the sensor coupler is configured in the form of a ball stud for ball joint at a side of the handle, the X-ray receiver is provided on an inner side of a surface thereof with a bearing coupled to the ball stud, and the ball stud and the bearing are coupled to allow the X-ray receiver to be rotatable relative to the handle.

10. The hand-grip type oral X-ray device of claim 8, wherein the sensor coupler has a hinge structure that allows the X-ray receiver to be rotated in a range of 90 degrees to −90 degrees relative to the handle.

11. The hand-grip type oral X-ray device of claim 1, wherein the handle comprises at least one of a configuration in which a part or entirety of the grip is configured to be bendable and a configuration in which the extension arm is configured to be bendable.

12. The hand-grip type oral X-ray device of claim 1, wherein the power supply unit is configured by selecting any one of a battery and a supercapacitor, and the power supply unit comprises a power charging unit configured to charge the power supply unit.

13. The hand-grip type oral X-ray device of claim 9, wherein the sensor coupler has a hinge structure that allows the X-ray receiver to be rotated in a range of 90 degrees to −90 degrees relative to the handle.

* * * * *